United States Patent
Blom

(10) Patent No.: US 7,975,696 B2
(45) Date of Patent: Jul. 12, 2011

(54) VOICE PROSTHESIS DILATOR/SIZER

(75) Inventor: Eric D. Blom, Carmel, IN (US)

(73) Assignee: Helix Medical, LLC, Plymouth, MI (US)

( * ) Notice: Subject to any disclaimer, the term of this patent is extended or adjusted under 35 U.S.C. 154(b) by 0 days.

(21) Appl. No.: 12/102,075

(22) Filed: Apr. 14, 2008

(65) Prior Publication Data

US 2009/0259309 A1    Oct. 15, 2009

(51) Int. Cl.
*A61M 16/00* (2006.01)
*A61F 2/20* (2006.01)

(52) U.S. Cl. ......... 128/207.29; 128/200.26; 128/207.14; 128/207.15; 128/207.16; 623/9

(58) Field of Classification Search ............ 623/9; 128/207.14–207.16, 200.26, 200.24, 207.29
See application file for complete search history.

(56) References Cited

U.S. PATENT DOCUMENTS

| | | | |
|---|---|---|---|
| 4,435,853 A | 3/1984 | Blom et al. | |
| 4,439,872 A * | 4/1984 | Henley-Cohn et al. | 623/9 |
| 4,614,516 A | 9/1986 | Blom et al. | |
| 4,820,304 A * | 4/1989 | Depel et al. | 623/9 |
| 4,911,716 A | 3/1990 | Blom et al. | |
| 5,078,743 A | 1/1992 | Mikalov et al. | |
| 5,197,465 A * | 3/1993 | Montgomery | 128/207.29 |
| 5,300,119 A * | 4/1994 | Blom | 623/9 |
| 5,353,787 A * | 10/1994 | Price | 128/200.26 |
| 5,391,205 A | 2/1995 | Knight | |
| 5,480,432 A * | 1/1996 | Suding et al. | 623/9 |
| 5,507,809 A | 4/1996 | Blom | |
| 6,494,848 B1 * | 12/2002 | Sommercorn et al. | 600/587 |
| 6,637,435 B2 * | 10/2003 | Ciaglia et al. | 128/207.29 |
| 6,764,453 B2 * | 7/2004 | Meier | 600/587 |
| 7,097,802 B2 * | 8/2006 | Brain | 264/255 |
| RE39,923 E | 11/2007 | Blom | |
| 7,921,847 B2 * | 4/2011 | Totz | 128/207.15 |

(Continued)

FOREIGN PATENT DOCUMENTS

DE    102004026316 B3    6/2005

(Continued)

OTHER PUBLICATIONS

Inhealth Technologies. "Voice Prostheses Accessories". Downloaded from <http://www.inhealth.com/featuredprdypacc1new.htm> using Way Back Machine on <www.archive.org> for publication date of Apr. 5, 2005 (2 pages).*

(Continued)

*Primary Examiner* — David Isabella
*Assistant Examiner* — Andrew Iwamaye
(74) *Attorney, Agent, or Firm* — Ronald W. Wangerow, Esq.; Harness, Dickey & Pierce, P.L.C.

(57) ABSTRACT

A voice prosthesis dilator and sizer device is provided including an elongated member having a first end with a tip and a flange and a second end with a stop portion. The elongated member includes an intermediate portion with a measuring area disposed adjacent to the flange and including measuring indicia thereon and having a dilation area adjacent to the second end. The elongated member also includes a recessed region adjacent to the flange to receive the flange in a folded position upon insertion into the non-dilated fistula. The dilation area has a larger diameter than the measuring area.

14 Claims, 2 Drawing Sheets

U.S. PATENT DOCUMENTS

| | | | | |
|---|---|---|---|---|
| 2002/0066453 A1* | 6/2002 | Ciaglia et al. | ............ | 128/207.29 |
| 2004/0187872 A1* | 9/2004 | Brain | ................ | 128/207.14 |
| 2004/0187941 A1 | 9/2004 | Seder et al. | | |
| 2005/0103332 A1* | 5/2005 | Gingles et al. | ............ | 128/200.24 |
| 2009/0320854 A1* | 12/2009 | Cuevas et al. | ............ | 128/207.29 |

FOREIGN PATENT DOCUMENTS

| | | | |
|---|---|---|---|
| WO | 97/41807 A1 | 11/1997 | |

OTHER PUBLICATIONS

Stratmed. "Stratmed: Distributor of Surgical Implants and Instruments". Downloaded from <http://www.stratmed.co.za/e2.htm> using Way Back Machine on <www.archive.org> for publication date of Jan. 20, 2005 (3 pages).*

Clinical Insights; InHealth Technologies; http://www.inhealth.com/educationalresourcesclininstghts.htm; (p. 1-11).

Blom-Singer Voice Prostheses; InHealth Technologies; http://www.inhealth.com/featuredprdvppage1new.htm; (p. 1-4).

Voice Prostheses Accessories; InHealth Technologies; http://www.inhealth.com/featuredprdvpacc1new.htm; (p. 1-3).

Blom-Singer Voice Restoration Systems; InHealth Technologies; 37-365-01 Rev. D; (21 pages).

The Provox System; Atos Medical; Cat. 2006/2007; (36 pages).

* cited by examiner

VOICE PROSTHESIS DILATOR/SIZER

FIELD

The present disclosure relates to a combined voice prosthesis dilator and sizer device.

BACKGROUND AND SUMMARY

The statements in this section merely provide background information related to the present disclosure and may not constitute prior art.

A voice prosthesis is a one-way valve placed into a puncture between the trachea and the esophagus of a user who cannot speak following surgical removal of the larynx (voicebox). The voice prosthesis allows air to flow from the lungs through the trachea and into the esophagus to enable voice/speech. Flanges at both ends of the voice prosthesis retain the prosthesis in the tracheoesophageal puncture. Prior to voice prosthesis insertion, a dilator has been used to prevent the puncture from closing, eliminate leakage of the esophageal content and to dilate the puncture prior to initial insertion and later re-insertion of the voice prosthesis. An exemplary known dilator device is a BLOM-SINGER® tracheoesophageal puncture dilator available from InHealth Technologies, a division of Helix Medical, LLC.

After removal of a surgical catheter or voice prosthesis, the dilator maintains the open fistula. Once inserted, the dilator is taped in place on the neck. This device is then removed after several minutes of dilation. Once the fistula is dilated, it needs to be sized. A voice prosthesis sizer, such as the BLOM-SINGER® voice prosthesis sizer available from InHealth Technologies, a division of Helix Medical, LLC, is placed on an inserter and the device is inserted into the fistula. The sizer is gently withdrawn until resistance is detected indicating that the esophageal collar is seated against the interior wall of the esophagus. The size is then read at the mark closest to the puncture entrance. After sizing, a voice prosthesis is then inserted into the puncture for voicing.

The voice prosthesis dilator and sizer device, according to the principles of the present disclosure, combines the functions of the separate voice prosthesis dilator and the sizer into a single device in order to provide a dilating and sizing function that is gentler on the fistula in that only one insertion is needed rather than two. Furthermore, the device makes the process easier for the clinician having only one device to handle. Furthermore, the use of a single device also reduces the chances for infection.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4 is a schematic illustration of a soluble retainer retaining the flanges in a folded position.

DETAILED DESCRIPTION

The following description is merely exemplary in nature and is not intended to limit the present disclosure, application, or uses.

Figure 1:
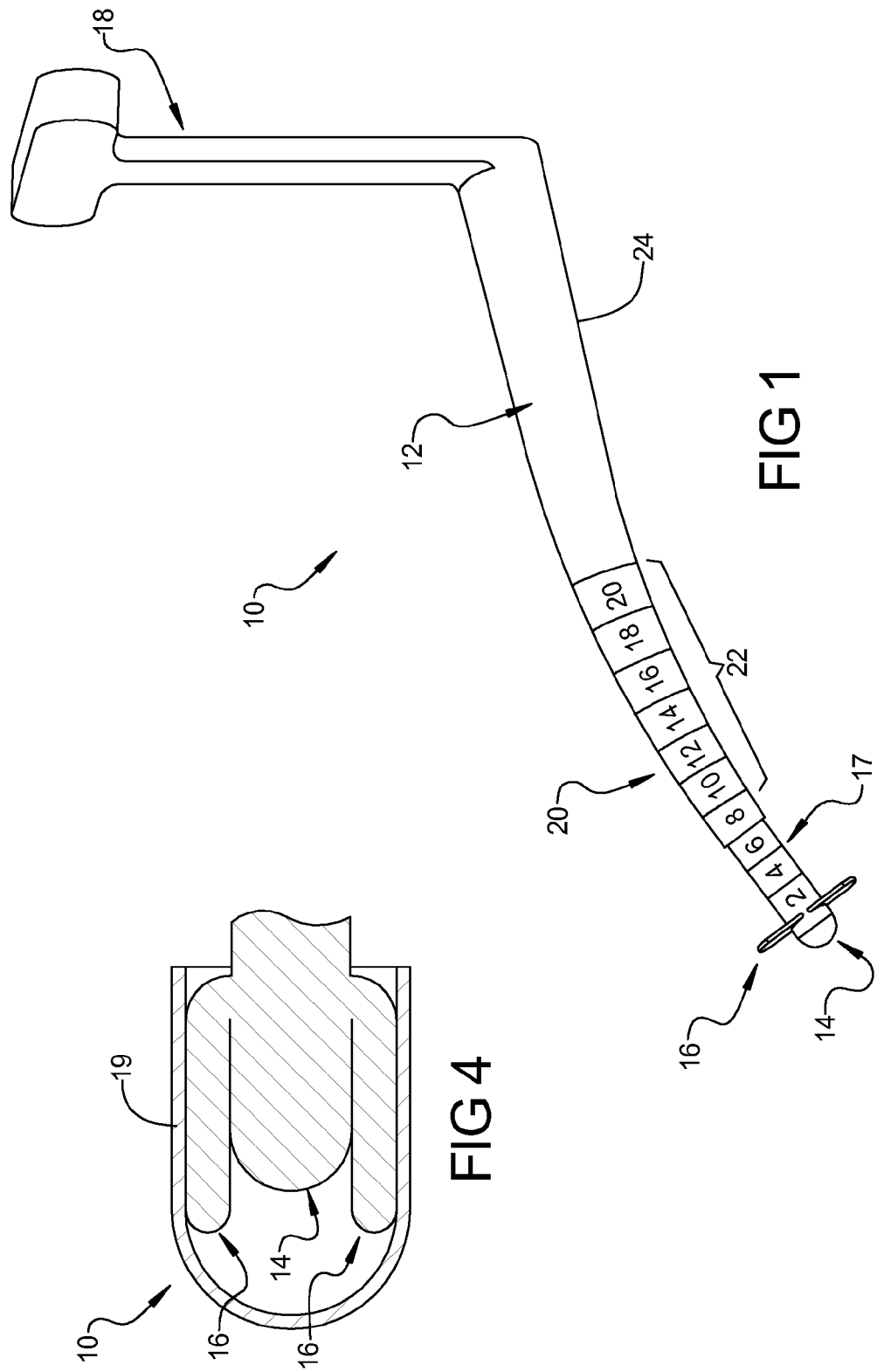
FIG. 1 is a perspective view of a voice prosthesis dilator and sizer device according to the principles of the present disclosure.

With reference to FIG. 1, a voice prosthesis and sizer device 10 will now be described. The voice prosthesis dilator and sizer device 10 includes an elongated member 12 having a first end with a tip 14 and a flange 16. The tip 14 can be rounded to facilitate insertion in the fistula (F), and the flange 16 can be annular or discontinuous so long as it provides the ability to detect a resistance upon withdrawal to indicate contact with the anterior wall of the esophagus. A second end of the elongated member includes a second end having a stop portion 18 extending generally transverse thereto. By "generally transverse," it is meant that the stop portion extends at an angle between 70 and 130 degrees relative to the elongated member 12 although other angles may be utilized.

The flange 16 can include one or more radially extending flange 16 and the elongated member 12 can include a recess region 17 adjacent each flange 16 to allow the flanges 16 to fold into the recess regions 17 upon insertion into the fistula (F) so that the flanges 16 can be received generally flush with the elongated member 12. Alternatively, as shown in FIG. 4, the flange or flanges 16 can be retained by a soluble retainer 19 in a folded position in order to facilitate insertion in a fistula. After insertion, the soluble retainer 19 can be dissolved by saliva or another fluid to allow the folded flange or flanges 16 to be deployed. The soluble retainer can include a gel cap such as that disclosed in U.S. Re. 39,923 or can include a soluble ring, band, or string.

The elongated member 12 includes an intermediate portion having a measuring area 20 disposed adjacent to the flange 16 and including measuring indicia 22 thereon. The measuring indicia can include numerical, alphabetical, or other graphical indicia along with markings that allow a clinician to measure the dimension (length) of the fistula from the back wall of the trachea and the front wall of the esophagus for appropriate prosthesis sizing.

A dilation area 24 is provided on the elongated member adjacent to the second end of the elongated member and adjacent to the stop portion 18. The dilation area 24 can have a larger diameter than the measuring area 20 and is appropriately sized so as to dilate the fistula or tracheoesophageal puncture to a desired dimension (diameter). More particularly, the dilation area 24 preferably has a diameter of two French larger than a desired prosthesis diameter, and more particularly, between 14 and 24 French. More specifically, voice prosthesis having a diameter of, for example, 16 French would typically require an 18 French dilator while a 20 French diameter prosthesis would require a 22 French dilator. An 18 French dilator can have a 12 French tip with gradually increasing diameter to the 18 French dilation area. A 22 French dilator can have a 16 French tip which gradually increases in diameter to the 22 French dilation area. The above dimensions are provided for exemplary purposes only and it should be understood that other larger and smaller diameters may also be utilized depending upon specific applications.

The voice prosthesis dilator and sizer device 10 can be made from an elastomeric or plastic material such as (but not limited to) silicone, PVC, polyurethane, polyolefins, or rubber. The device 10 is preferably made from a material that is deformable so as to be comfortably inserted into the fistula without being too rigid so as not to conform with the shape of the fistula and esophagus in which it is inserted. The material is also preferably rigid enough so as to facilitate insertion through the fistula and into the esophagus as described above.

The stop portion 18 can include a T-shape that prevents the device from being inserted too far into the esophagus and fistula. The stop portion 18 can be taped to the user's neck while the dilation area 24 is in the fistula for dilating the fistula. Taping the stop portion 18 in place prevents the device 10 from being inadvertently moved relative to its desired position during the dilation stage.

Figure 2:
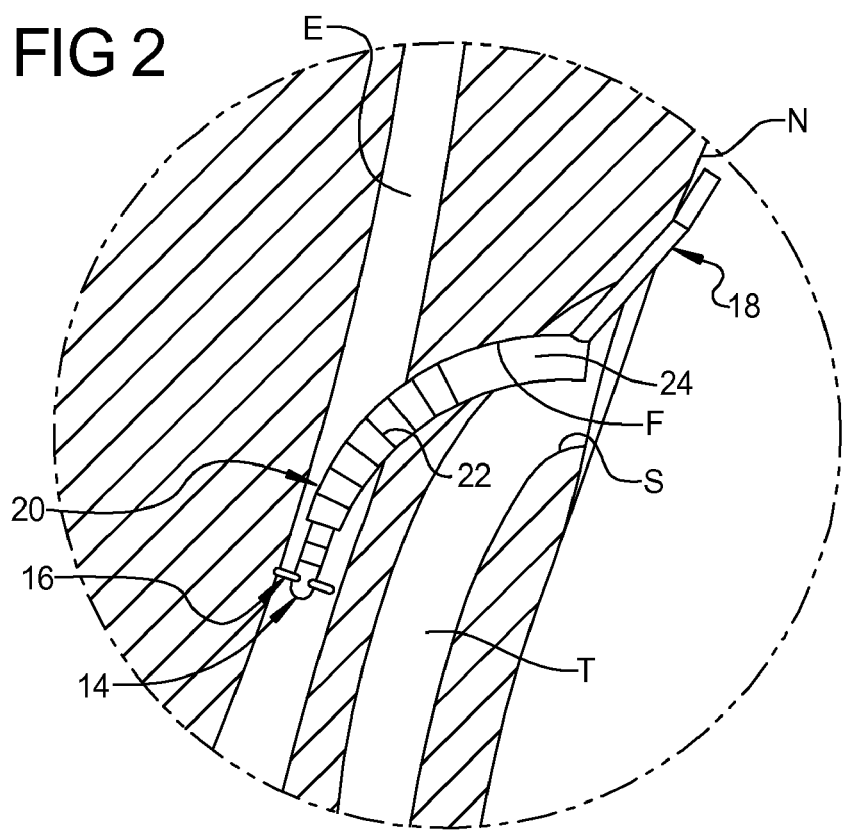
FIG. 2 is a schematic illustration of the voice prosthesis dilator and sizer device inserted into a fistula of a patient in order to dilate the fistula for allowing easier insertion of a voice prosthesis.
Figure 3:
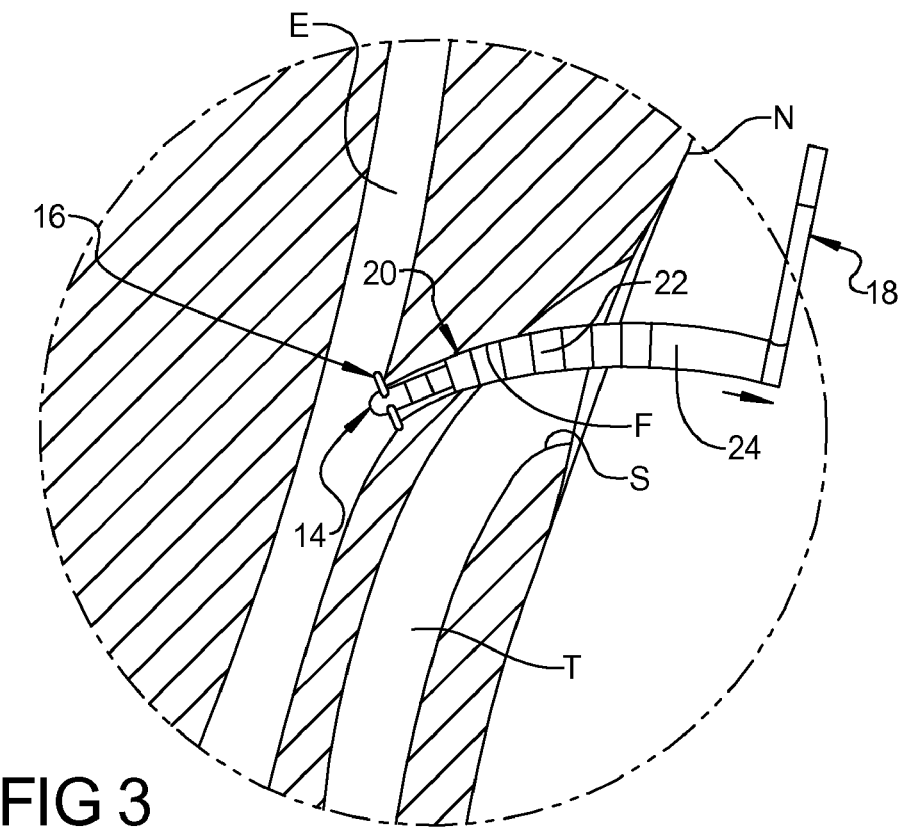
FIG. 3 is a schematic illustration of the voice prosthesis dilator and sizer device utilized for sizing the fistula to facilitate selection of the appropriate sized voice prosthesis device.

As illustrated in FIG. 2, the voice prosthesis dilator and sizer device 10 is shown inserted into the fistula (F) of the patient in order to dilate the fistula (F) for later insertion of a voice prosthesis device. Upon insertion into the fistula (F), the flanges 16 can fold rearward into the recess regions 17 to facilitate easier insertion into the non-dilated fistula (F). In the position shown in FIG. 2, the tip 14 of the device 10 is inserted into the esophagus (E) via the fistula (F) that is defined by a puncture that extends between the trachea (T) and the esophagus (E). The trachea (T) is provided with a stoma (S) or opening through the user's neck into the trachea (T), as shown. The dilation area 24 of the device 10 is received in the fistula (F) in order to dilate the fistula (F) in a manner as described above. The stop portion 18 can be taped to the user's neck (N) in order to secure the device 10 in place. After the device has been inserted for several minutes, the fistula (F) is properly dilated and the device 10 is withdrawn as illustrated in FIG. 3 until the flange 16 engages the anterior wall of the esophagus (E). At this point, the clinician can utilize the measuring indicia 22 on the measuring area 20 by selecting the measuring indicia 22 that is closest to the puncture entrance of the fistula (F), thus measuring the distance between the posterior wall of the trachea (T) and the anterior wall of the esophagus (E). The device 10 is then carefully removed from the fistula (F) and a properly sized voice prosthesis device is selected and then inserted into the fistula in order to provide voicing.

The voice prosthesis dilator and sizer device 10 of the present disclosure is gentler on the fistula and only one insertion is needed rather than two with the separately provided prior art devices. Furthermore, the use of the device is easier for the clinician since only one device is required to be handled and inserted into the fistula (F). Furthermore, the use of a single insertion device also reduces the risk of infection or damage to the fistula.

What is claimed is:

1. A voice prosthesis dilator and sizer device, comprising: a deformable elongated member having a first end with a tip and a flange and a second end with a stop portion that extends generally transverse to the longitudinal axis of said second end, said elongated member including an intermediate portion with a measuring area disposed adjacent to said flange and including measuring indicia thereon and having a dilation area adjacent said second end, said dilation area having a larger diameter than said measuring area, said measuring area extending from said flange along said intermediate portion and terminating prior to said dilation area, and said elongated member comprising a preformed arcuate shape in the axial direction, wherein said arcuate shape extends along substantially the entire longitudinal length of the measuring area.

2. The voice prosthesis dilator and sizer device according to claim 1, wherein said flange is spaced from said tip.

3. The voice prosthesis dilator and sizer device according to claim 1, wherein said measuring indicia extend axially along said measuring area.

4. The voice prosthesis dilator and sizer device according to claim 1, wherein said stop portion has a generally T-shape.

5. The voice prosthesis dilator and sizer device according to claim 1, wherein said dilation area has a diameter of between 14 and 24 French so as to fit within a tracheoesophageal puncture.

6. The voice prosthesis dilator and sizer device according to claim 1, wherein said tip is rounded.

7. The voice prosthesis dilator and sizer device according to claim 1, wherein said elongated member is made from one of an elastomeric or plastic material.

8. The voice prosthesis dilator and sizer device according to claim 1, wherein said elongated member includes a recessed region adjacent to said flange for receiving said flange in a folded position.

9. The voice prosthesis dilator and sizer device according to claim 1, further comprising a soluble retainer for retaining said flange in a folded position.

10. A method of dilating and sizing a puncture between a trachea and an esophagus, comprising;
    inserting into the puncture opening a deformable elongated member having a first end with a tip and a retention flange and a second end with a stop portion that extends generally transverse to the longitudinal axis of said second end, said elongated member including an intermediate portion with a measuring area disposed adjacent to said retention flange and including measuring indicia thereon and having a dilation area adjacent said second end, said dilation area having a larger diameter than said measuring area and said dilation area being received in said puncture opening for a period of time sufficient to dilate the puncture opening to ease insertion of a voice prosthesis, said measuring area extending from said flange along said intermediate portion and terminating prior to said dilation area, and said elongated member comprising a preformed arcuate shape in the axial direction, wherein said arcuate shape extends along substantially the entire longitudinal length of the measuring area;
    withdrawing said elongated member until resistance is detected indicating that the flange is seated against an anterior wall of the esophagus;
    reading the measuring indicia at a location closest to the puncture opening; and
    removing the elongated member from the puncture opening.

11. A voice prosthesis dilator and sizer device, comprising: a deformable elongated member having a first end with a rounded tip and a flange and a second end with a stop portion that extends generally transverse to the longitudinal axis of said second end, said elongated member including a recessed region disposed adjacent said tip, an intermediate portion disposed adjacent to said recessed region and a dilation area between said intermediate portion and said second end, said dilation area having a larger diameter than said intermediate portion and said intermediate portion having a larger diameter than said recessed region, said recessed region and said intermediate portion including a measuring area having measuring indicia thereon between said flange and said dilation area, said measuring area extending from said flange beyond said recessed region along said intermediate portion and terminating prior to said dilation area, and said elongated member comprising a preformed arcuate shape in the axial direction, wherein said arcuate shape extends along substantially the entire longitudinal length of the measuring area.

12. The voice prosthesis dilator and sizer device according to claim 11, wherein said stop portion has a T-shape.

13. The voice prosthesis dilator and sizer device according to claim 11, wherein said recessed region is configured to receive said flange in a folded position.

14. The voice prosthesis dilator and sizer device according to claim 11, wherein said recessed region has a longitudinal length less than said intermediate portion.

* * * * *